United States Patent [19]
Koike et al.

[11] Patent Number: 5,122,991
[45] Date of Patent: Jun. 16, 1992

[54] DISTANCE MEASURING APPARATUS AND METHOD

[75] Inventors: Masahiro Koike; Sigeru Kajiyama; Toshiyuki Furukawa; Kazuo Takaku; Toshiyuki Sawa, all of Hitachi, Japan

[73] Assignee: Hitachi, Ltd., Tokyo, Japan

[21] Appl. No.: 551,476

[22] Filed: Jul. 12, 1990

[30] Foreign Application Priority Data

Jul. 14, 1989 [JP] Japan .................. 1-180210

[51] Int. Cl.$^5$ ............................................ G01S 3/801
[52] U.S. Cl. ...................................... 367/127; 73/597
[58] Field of Search ............... 73/597, 602, 619, 626, 73/637, 638, 641, 633, 634; 367/120, 127, 129

[56] References Cited

U.S. PATENT DOCUMENTS

| 3,988,922 | 11/1976 | Clark et al. | 73/637 |
| 4,010,636 | 3/1977 | Clark et al. | |
| 4,160,386 | 7/1979 | Jackson et al. | 73/633 |
| 4,442,713 | 4/1984 | Wilson et al. | 73/626 |
| 4,446,740 | 5/1984 | Wilson et al. | 73/626 |
| 4,914,642 | 4/1990 | Fraser et al. | 367/129 |

FOREIGN PATENT DOCUMENTS

| 51-95888 | 8/1976 | Japan | 73/637 |
| 0102580 | 6/1985 | Japan | . |
| 0102581 | 6/1985 | Japan | . |
| 0233579 | 11/1985 | Japan | 367/129 |
| 1291157 | 11/1989 | Japan | . |

Primary Examiner—Hezron E. Williams
Assistant Examiner—Rose M. Finley
Attorney, Agent, or Firm—Antonelli, Terry Stout & Kraus

[57] ABSTRACT

A distance measuring apparatus and method using an acoustic signal. It includes a transmitting probe for transmitting an acoustic signal from a transmitter, a plurality of receiving probes having resonance frequencies different from the central frequency of the signal transmitted from the transmitting probe, and a control circuit for controlling the functions of those probes. The acoustic signal is received by a receiving probe having a resonance frequency which provides the maximum received-signal sensitivity at the central frequency of the received acoustic signal under the control of the control circuit to thereby measure a long distance accurately.

16 Claims, 18 Drawing Sheets

F I G. 8A
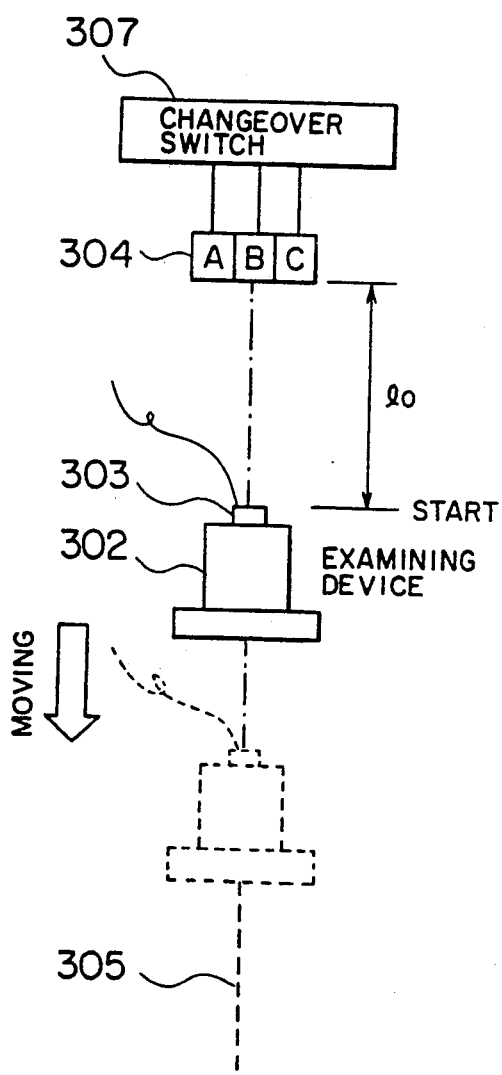
F I G. 8B
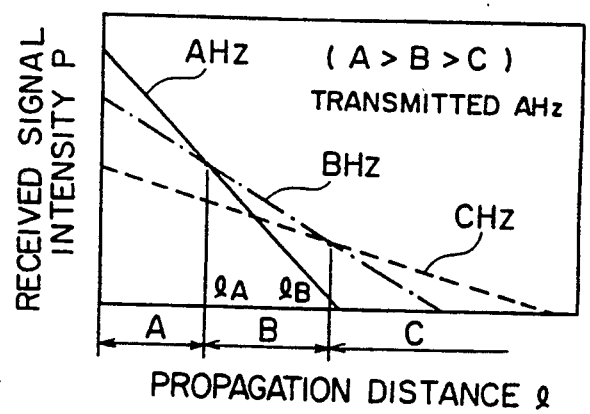
F I G. 8C
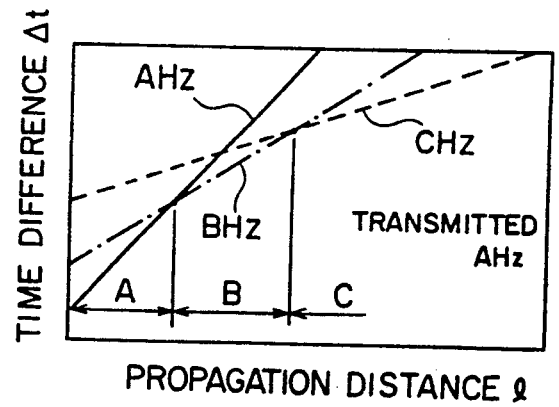

RECEIVED AHz

RECEIVED BHz ($\ell_1 < \ell_2$)

DISTANCE MEASURING APPARATUS AND METHOD

BACKGROUND OF THE INVENTION

The present invention relates to distance measuring apparatus using an acoustic signal and more particularly to apparatus provided additionally in a non-destructive examination equipment for measuring a long distance, for example, to an objective.

Usually, a large-sized pressure vessel is formed by welding thick steel plates. When the pressure vessel cannot be observed visually due to the coverage of the vessel with a thermal insulation material, a shielding wall, etc., an examination equipment is used which includes a vehicle with magnetic wheels and caterpillars of a magnetic material and a device mounted on the vehicle for examining the weld in a non-destructive manner to confirming whether the weld in the vessel is complete or not. The wall surface vehicle for examination examines the weld along the welding line.

In the non-destructive examination, it is necessary to accurately measure the position of the vehicle for an examination of a vessel examination equipment. Such techniques are disclosed, for example, in JP-A-51-95888 (corresponding to U.S. Pat. Nos. 3,988,922; and 4,010,636), JP-A-60-102580 and 60-102581 related to each other, and JP-A-1-291157.

FIG. 21 schematically illustrates the disposition of the vehicle for the examination of a vessel examination equipment (assume that the device is not of a self-propelled type for convenience of explanation in FIG. 21) for measuring the position of the device using an acoustic signal. In FIG. 21, broken lines show a weld (line) to be examined.

For example, an examining device 802 is set on a pressure vessel 1. A transmitting probe 803 as position detecting means attached to the examining device transmits an acoustic signal 805 having a frequency, for example, of 350 KHz from the vessel surface into the vessel. The acoustic signal 805 propagates through the vessel at a well-known sound velocity and is received by a receiving probe 804 fixed to the vessel at a time corresponding to the distance. Thus, the distance between the receiving probe 804 and the transmitting probe 803 (examining device) is measured.

When the distance between two points is measured using an acoustic signal, generally, the transmitting probe and the receiving probe use the same-frequency signal. As the transmission frequency increases, the attenuation coefficient increases and the acoustic signal does not arrive at a distant point. Therefore, it is technically difficult to use an acoustic signal having a high frequency to measure the position of the examining vehicle on a large-sized pressure vessel. However, conversely, the measuring accuracy on the propagation distance increases as the frequency used increases.

In the JP-A-51-95888 techniques, a low frequency (350 KHz) is used to cause the acoustic signal to arrive at a distant point. Therefore, the measurement of a propagation distance with high accuracy is difficult.

SUMMARY OF THE INVENTION

It is an object of the present invention to provide a distance measuring apparatus and method which is capable of using a high frequency acoustic signal for transmission by receiving the acoustic signal at all times using a receiving probe the resonance frequency of which is the central frequency of the acoustic signal which arrives at the receiving probe, and which is capable of receiving the acoustic signal with high reception sensitivity at a distant point and measuring the (propagation) distance between the transmitting probe and the receiving probe with high accuracy.

According to the present invention, if a surface wave of 5 kHz is used for transmitting purposes, a 2.25 MHz-receiving probe provides a reception sensitivity which is 14 dB high and a measuring accuracy which is 50% high compared to a 5 MHz-receiving probe at 600 mm distance.

In order to achieve the above object, the present invention provides a distance measuring apparatus comprising:

a transmitting probe for transmitting an acoustic signal from a transmitter;

a plurality of receiving probes capable of receiving the signal; and means for controlling the function of the transmitting probe and the plurality of receiving probes, wherein at least one of the plurality of receiving probes has a reconance frequency different from the central frequency of the frequencies of a signal transmitted by the transmitting probe.

The frequency distribution of the acoustic signal transmitted by the transmitting probe changes as the signal propagates because the proportion of distance attenuation differ depending on frequency. Therefore, a frequency in the frequency distribution at which the intensity of the signal component becomes maximum at the position where the distance is measured differs from that at the transmission. In the present invention, the acoustic signal is received by the receiving probe which uses as its resonance frequency a frequency at which the intensity of the signal component becomes maximum. Thus, since the received signal intensity becomes maximum, the acoustic signal is received with high reception sensitivity even at a distant point to thereby improve the distance measuring accuracy.

The relationship between the intensity, frequency and propagation distance of the transmitted acoustic signal will be described in more detail. FIG. 13 shows a frequency distribution curve. As shown in FIG. 13, with a pulse wave used for measuring a propagation distance, etc., the frequency of the transmitted acoustic signal has any extension with a certain frequency as the center which is referred hereinafter to as a central frequency A, which is not the central frequency between the highest and lowest frequencies used, but the frequency where the frequency distribution becomes a peak where the axis of abscissas denotes frequency f and the axis of ordinates the intensity g(f) for each of the frequencies of the transmitted acoustic signal. As the acoustic signal propagates, its intensity is attenuated due to scattering, etc. The percentage of attenuation per unit propagation distance (hereinafter referred to as an attenuation coefficient) increases as the frequency increases. FIG. 14 shows a curve of the relationship between frequency, received signal intensity and propagation distance. Therefore, the intensity of the acoustic signal decreases as the frequency increase and the distance increase. This relationship is shown by FIG. 14. A distribution of attenuation of the respective frequencies for the propagation distance is represented by h(f,l).

When an acoustic signal having a central frequency of A in a frequency distribution of g(f) is transmitted, the frequency distribution of F(f,l) at a distance of l is given by $$F(f,l) = g(f) \cdot h(f,l) \qquad (1)$$

The F(f,l) is shown in FIG. 15 from which it will be seen that the frequency fm at which the F(f,l) becomes maximum varies depending on the propagation distance of l. Therefore, if the acoustic signal is received by the receiving probe which uses as the resonance frequency the maximum frequency of fm of the F(f,l), the received signal intensity becomes maximum. In other words, this means the acoustic signal is received with the maximum intensity by changing the resonance frequency of the receiving probe depending on propagation distance.

The frequency distribution of R(f,l) of the received wave at a distance of l is given by $$R(f,l) = F(f,l) \cdot k(f) = g(f) \cdot h(f,l) \cdot k(f) \qquad (2)$$

where k(f) is the frequency distribution of the receiving probe.

The above relationship will be described more specifically by taking position detection by a wall surface vehicle for an examination as an example. When the receiving probe 504 receives an acoustic signal transmitted by a transmitting probe 503 provided in the wall surface vehicle 502 into a sample 501, the relationship between the transmitted wave and the received wave is shown in FIG. 16 which simulates the measurement of the travel distance. The propagation distance or the distance of l between the transmitting probe 503 and the receiving probe 504 is obtained from the product of the time T required from transmission to a rising of the received wave and the propagation velocity v of the acoustic signal in the object 501 follows:

$$l = T \cdot v \qquad (3)$$

FIGS. 17A and 17B show the waveforms of a transmitted acoustic signal having a frequency of A Hz received by two kinds of receiving probes having resonance frequencies of A and B Hz where A is larger than B and disposed at distances of $l_1$ and $l_2$ ($l_1$ is less than $l_2$). FIG. 17A shows the waveforms received by a receiving probe having a resonance frequency of A Hz and disposed at distances of $l_1$ and $l_2$ and shown by the solid and broken lines, respectively. Similarly, FIG. 17B shows the waveforms received by a receiving probe having a resonance frequency of B Hz.

As will be seen in FIGS. 17A and 17B, the received signal intensity obtained by the receiving probe having the resonance frequency of A Hz at the distance of $l_1$ is higher than that obtained by the receiving probe having the resonance frequency of B Hz. However, as the frequency increases, the attenuation coefficient increases, so that the received signal intensity by the receiving probe for B Hz is higher at a longer distance of $l_2$ than that by receiving probe for A Hz.

The propagation time, namely, the time from the start of the transmission to a rising of the received waveform corresponds to the propagation distance, as mentioned above. Automatic detection of a rising of the received waveform is difficult due to noise, etc. Actually, the time from the start of the transmission to a time where the threshold value involving the elimination of noise is exceeded is used as the propagation time. In this case, as shown in FIGS. 17A and 17B, the time of $\Delta t$ from a rising of the received waveform to the time where the threshold value is exceeded is an error in the propagation time. In FIGS. 17A and 17B, the receiving probe for A Hz has a higher received signal intensity and a rapider rise than the receiving probe for B Hz at the distance of $l_1$, so that the time difference $\Delta t$ is small; namely, $\Delta t_A l_1$ is less than $\Delta t_B l_1$. At the longer distance of $l_2$, the received signal intensities are reversed, so that the time of $\Delta t$ on the receiving probe having the resonance frequency of B Hz is smaller than that on the receiving probe having the resonance frequency of A Hz: namely, $\Delta t_A l_2$ is larger than $\Delta t_B l_2$.

FIGS. 18A and 18B schematically show the relationship between propagation distance of l and received signal intensity of P and the relationship between propagation distance of l and time difference of $\Delta t$, respectively. In FIGS. 18A and 18B, the transmission frequency is A Hz and receiving probes having resonance frequencies of A, B and C Hz where A > B > C are used for reception. As will be seen in FIGS. 18A and 18B, the use of receiving probes having resonance frequencies of A, B and C Hz for distances of zero to $l_A$, $l_A$ to $l_B$, and $l_B$ or more, respectively, provides corresponding higher received signal intensities, a smaller time difference of $\Delta t$ and smaller errors in the measurement. FIGS. 19A and 19B show the results of experimental study of the relationship. In the study, a surface wave having a central frequency of 5 MHz was used as a transmitted acoustic signal, and measurement was made for receiving probes having three resonance frequencies of 1, 2.25 and 5 MHz and for five kinds of distances of 0, 100, 200, 400 and 600 mm. (In FIGS. 19A and B, a black dot designates the results obtained by a 1 MHz-receiving probe, a white triangle designates the results obtained by a 2.25 MHz-receiving probe, and a black triangle designates the results obtained by a 5 MHz-receiving probe). The experimental results of FIGS. 19A and 19B coincide well with the indication of the schematic view of FIGS. 18A and 18B. While in the particular embodiment three kinds of receiving probes were used and discrete results were thus obtained, a continuous result would be obtained if many kinds of receiving probes are used. If the places where the receiving probes are installed are limited, two kinds of receiving probes having resonance frequencies of A, B Hz; A, C Hz; or B, C Hz may be used.

BRIEF DESCRIPTION OF THE DRAWINGS

These and other objects and advantages of the present invention will become apparent by reference to the following description and accompanying drawings wherein:

FIGS. 8A, 8B and 8C schematically illustrate a fourth embodiment;

FIG. 17A illustrates the waveform of a signal received by a receiving probe having a resonance frequency of A Hz, while FIG. 17B illustrates the waveform of a signal received by a receiving probe having a resonance frequency of B Hz;

FIGS. 18A illustrates the relationship between propagation distance of l and received signal intensity, while FIG. 18B illustrates the relationship between propagation distance of l and time difference of $\Delta t$;

DESCRIPTION OF THE PREFERRED EMBODIMENTS

Figure 1:
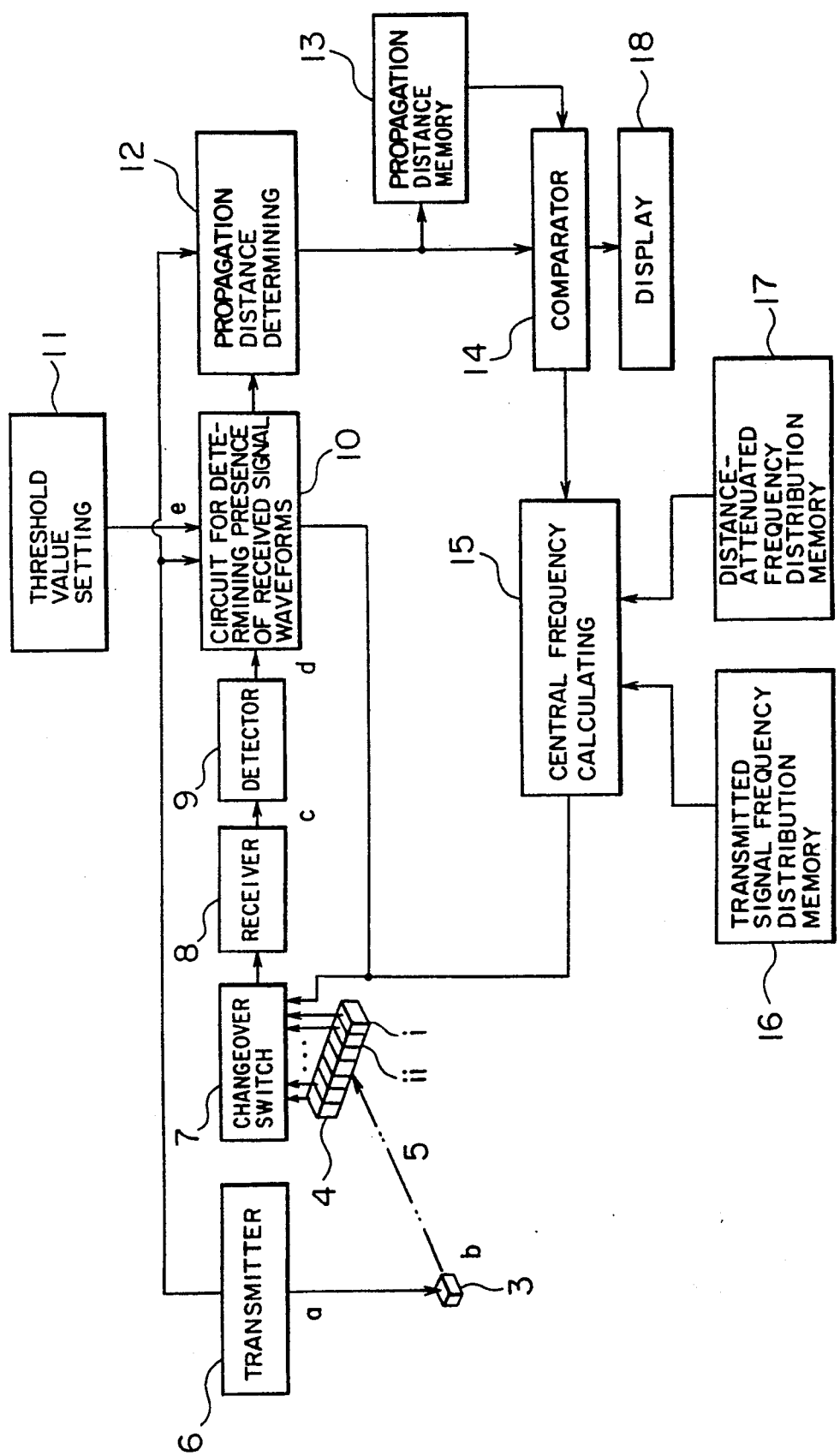
FIG. 1 schematically illustrates the structure of a first embodiment.

The present invention will now be described with reference to embodiments;

FIG. 1 is a schematic of a first embodiment of the present invention. In FIG. 1, reference numeral 3 denotes a transmitting probe; 4, a receiving probe (group); 5, an acoustic signal; 6, a transmitter; 7, a switch for selecting a receiving probe; 8, a receiver; 9, a detector; 10, a circuit for determining the presence of a received wave; 11, a threshold value setting circuit; 12, a propagation distance measuring circuit; 13, a propagation distance memory; 14, a comparator; 15, a central frequency calculating circuit; 16, a transmission signal frequency distribution memory; 17, a distance-dependent frequency attenuation distribution memory; and 18, a display.

Figure 20:
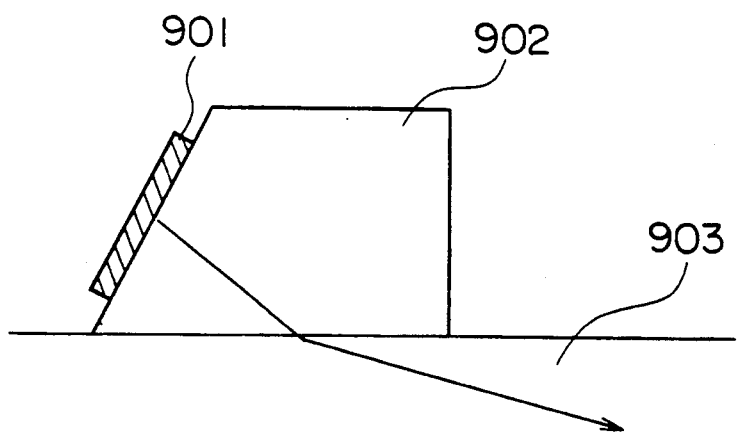
FIG. 20 illustrates a transmitting probe of an embodiment according to the present invention.
Figure 21:
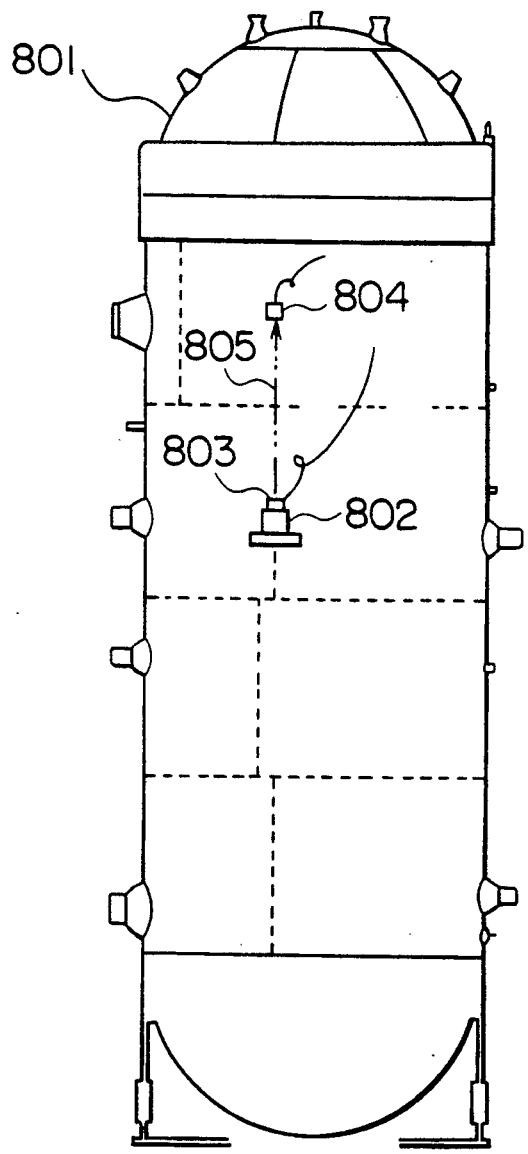
FIG. 21 illustrates a conventional examination equipment for a pressure vessel.

The structure of the transmitting probe 3 is shown in FIG. 20. Reference numeral 901 denotes a transducer of crystal, lead zirconate titanate or the like having piezoelectric effect. This transducer generates an acoustic signal when it is impressed with a voltage due to piezoelectric effect. A wedge 902, for example, of acrylic resin refracts ultrasonic waves, generated by the transducer, in accordance with Snell's law such that the refracted waves propagate as surface waves through the material 903 of the vessel in a parallel direction to material surface. It is desirable that a couplant such as water or glycerol paste (not shown) is provided between the wedge 902 and the material 903 to improve the propagation of the ultrasonic waves.

Since the receiving probe has a structure similar to that of the transmitting probe, and further detailed description and indication thereof will be omitted. When a voltage is applied across the transducer of the transmitting probe, it generates an acoustic signal while when the transducer of the receiving probe converts a received acoustic signal to an electrical signal (voltage).

The receiving probe(group) include a plurality of receiving probes which have resonance frequencies which are the same as, and lower than, the central frequency of a transmitted signal. The resonance frequency is previously obtained experimentally using a frequency distribution of g(f) of a transmitted acoustic signal and an attenuated distribution of h(f,l) of the frequencies depending on distance and set to a frequency which provides high received-signal sensitivity corresponding to the distance measured. A receiving probe of a different frequency is easily obtained by using a transducer having a different thickness.

Figure 2:
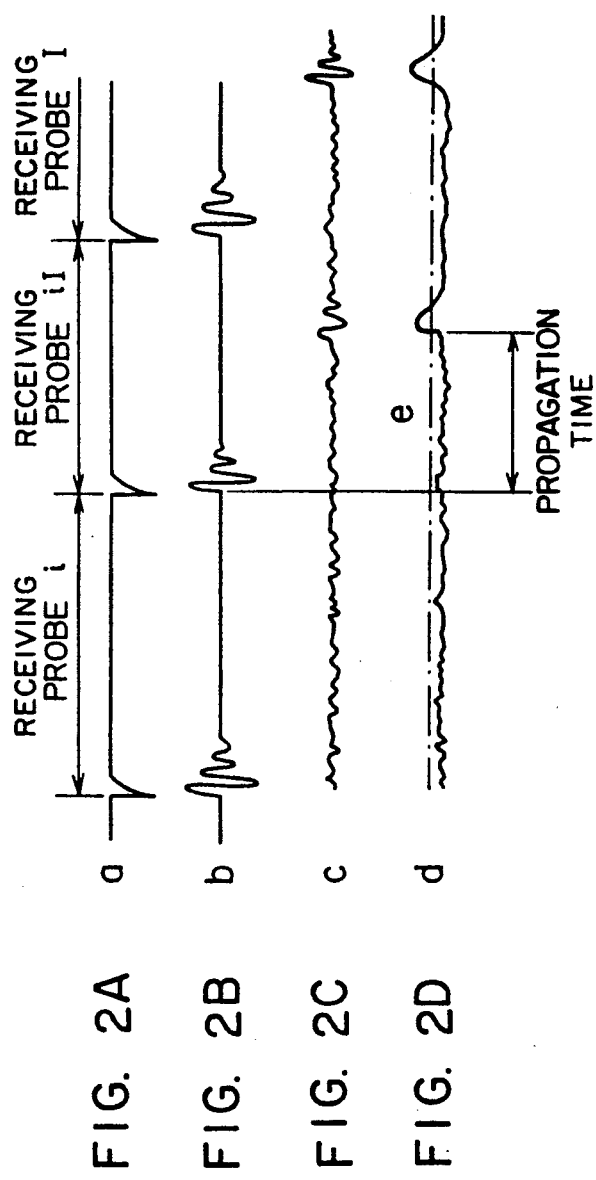
FIGS. 2A to 2D illustrate the waveforms of signals in FIG. 1.
Figure 3:
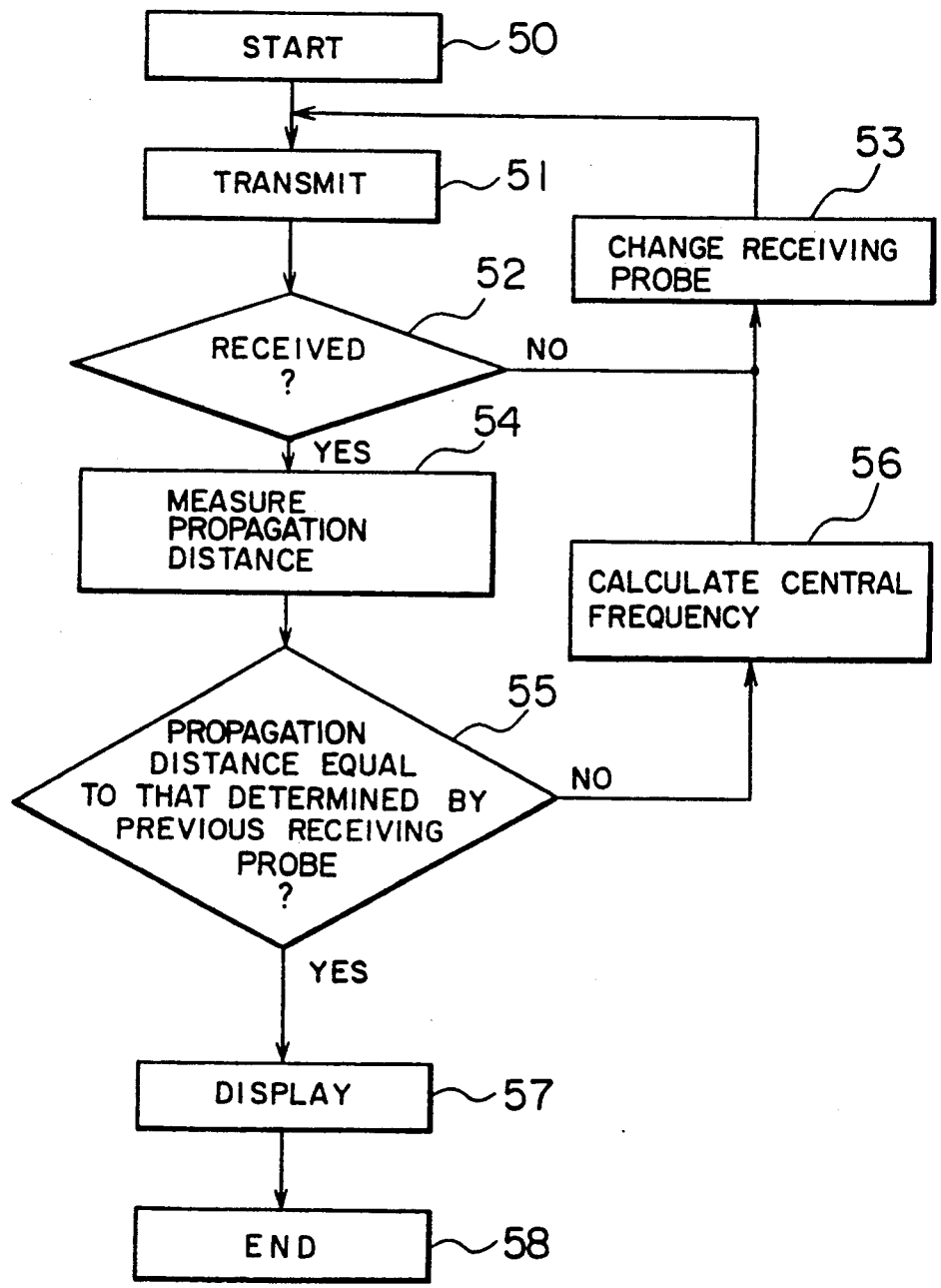
FIG. 3 is a flowchart directed to the embodiment of FIG. 1.

FIGS. 2A to 2D schematically illustrate the waveforms of signals at the respective stages of the first embodiment, and FIG. 3 is an operation flowchart.

The operation of the present embodiment will be described with reference to FIGS. 1 to 3.

Data on the frequency distribution g(f) of the transmitted acoustic signal and data on the attenuation distribution of h(f,l) of the frequencies depending on distance obtained when the resonance frequency of the receiving probe is determined are previously stored in the transmitted signal frequency distribution memory 16 and the distance-dependent frequency attenuation distribution memory 17. At the beginning, the receiver 8 is connected to a receiving probe i of the receiving probe group 4 via the switch 7. The propagation distance memory 13 is reset to 0. An acoustic signal 5 (FIG. 2B) is transmitted by the transmitting probe 3 in accordance with a transmitted signal a (FIG. 2A) from the transmitter 6 (step 51 in FIG. 3). The propagated acoustic signal is received by the receiving probe i and sent via the receiver 8 to the detector 9 (FIG. 2C). A received-wave presence determining circuit 10 determines whether the signal (FIG. 2D) obtained by detecting the RF signal with the detector 9 exceeds a threshold e (FIG. 2D) set by the threshold setting circuit 11 to eliminate noise previously (judging step 52 in FIG. 3). If a signal exceeding the threshold value is not received during the transmission interval for the acoustic signal, the receiving probe ii is selected by the switch 7 (step 53 in FIG. 3). The flow of the signal in the receiving probe ii is the same as that in the receiving probe i between the switch 7 and the received-signal presence determining circuit 10. The receiving probes iii, iv . . . are selected sequentially by the switch 7 until a received signal which is equal to, or higher than, the threshold value is obtained. For example, if the waves received by the receiving probe ii exceed the threshold, they are delivered to the propagation distance determining circuit 12 to measure the propagation distance of $l_1$ from the propagation time (step 54 in FIG. 3). The data on the propagation distance of $l_1$ is stored in the propagation distance memory 13. Simultaneously, they are delivered to the comparator 14 where they are compared with the data on the last propagation distance of $l_0$ (in this case, the initial value of $l_0=0$) stored in the propagation distance memory 13 (determination step 55 in FIG. 3). If the $l_1$ and $l_0$ are not equal, the data on the propagation distance of $l_1$ is delivered to the central frequency calculating circuit 15, values corresponding to the propagation distance of $l_1$ are read out of memories 16 and 17, and the central frequency of fm is calculated in accordance with the equation (1) (step 56 in FIG. 3 ). A receiving probe I having a resonance frequency equal to the central frequency of fm is selected (step 53). The receiving probe I is to receive signals exceeding the threshold. The flow of the signal from the switch 7 to the comparator 14 is the same as that in the case of the receiving probe ii. The comparator 14 compares $l_2$ and the data on the propagation distance of $l_1$ obtained by the receiving probe ii stored in the memory 13 where $l_2$ is the propagation distance from the receiving probe I obtained by the propagation distance measuring circuit 12 (step 55). If $l_1$ is equal to $l_2$, the data on the propagation distance $l_2$ is delivered to the display 18 for displaying purposes (step 57). If not, the data on $l_2$ is delivered to the central frequency calculating circuit 15 to obtain the central frequency of fm corresponding to $l_2$ (step 56). A receiving probe corresponding to the central frequency of fm is then selected and transmission is started. The subsequent procedures are the same as those taken in the case of the receiving probe I. The comparator 14 repeats its comparing operation until the propagation distance calculated now becomes equal to the data on the last propagation distance stored in the memory 13.

Whether another receiving probe is selected instead or the propagation distance is indicated and the procedures are terminated is performed by comparing the propagation distance. However, similar results can be obtained by comparing the central frequencies using a comparator provided between the central frequency calculating circuit 15 and the switch 7.

Figure 4:
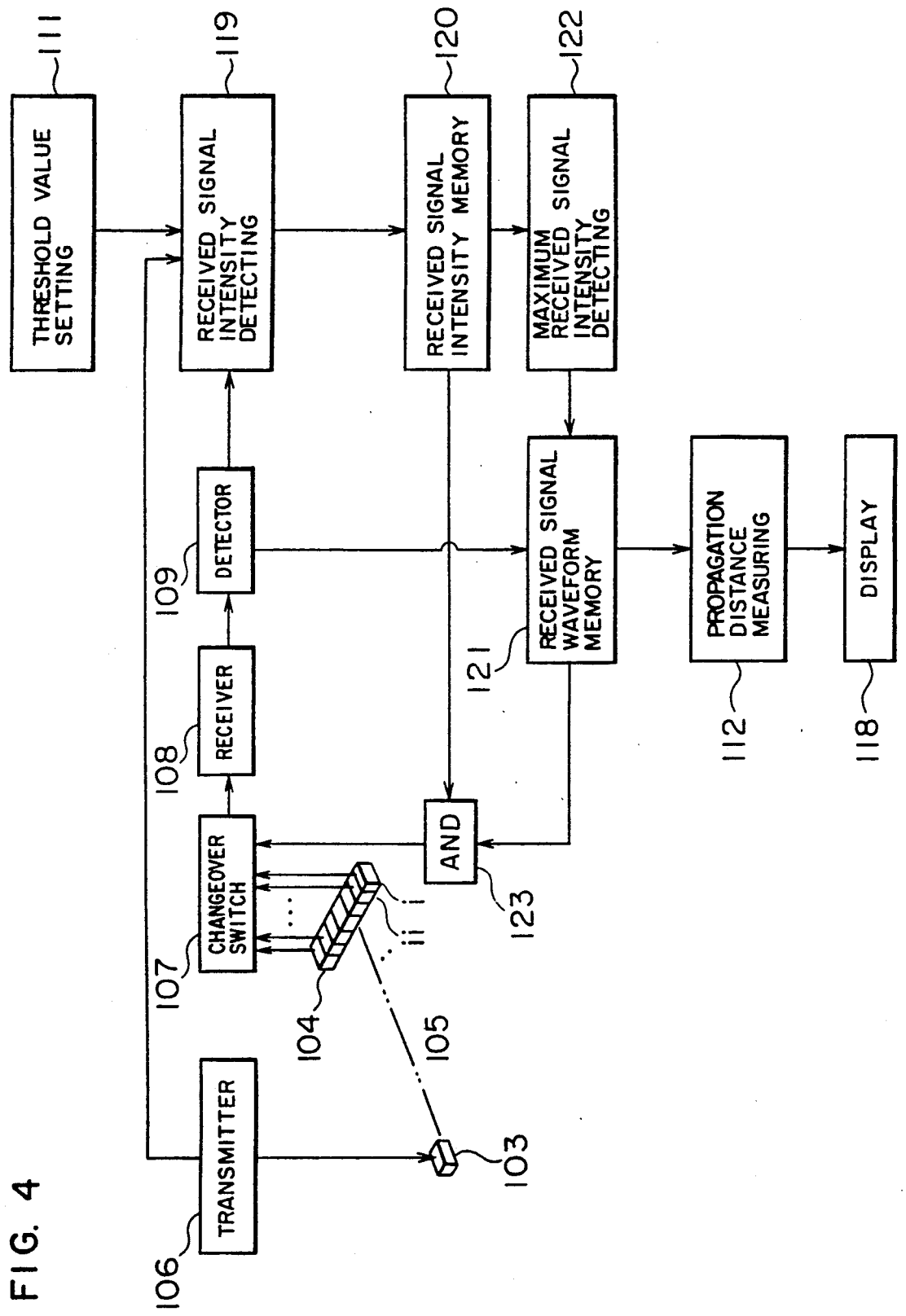
FIG. 4 schematically illustrates the structure of a second embodiment.
Figure 5:
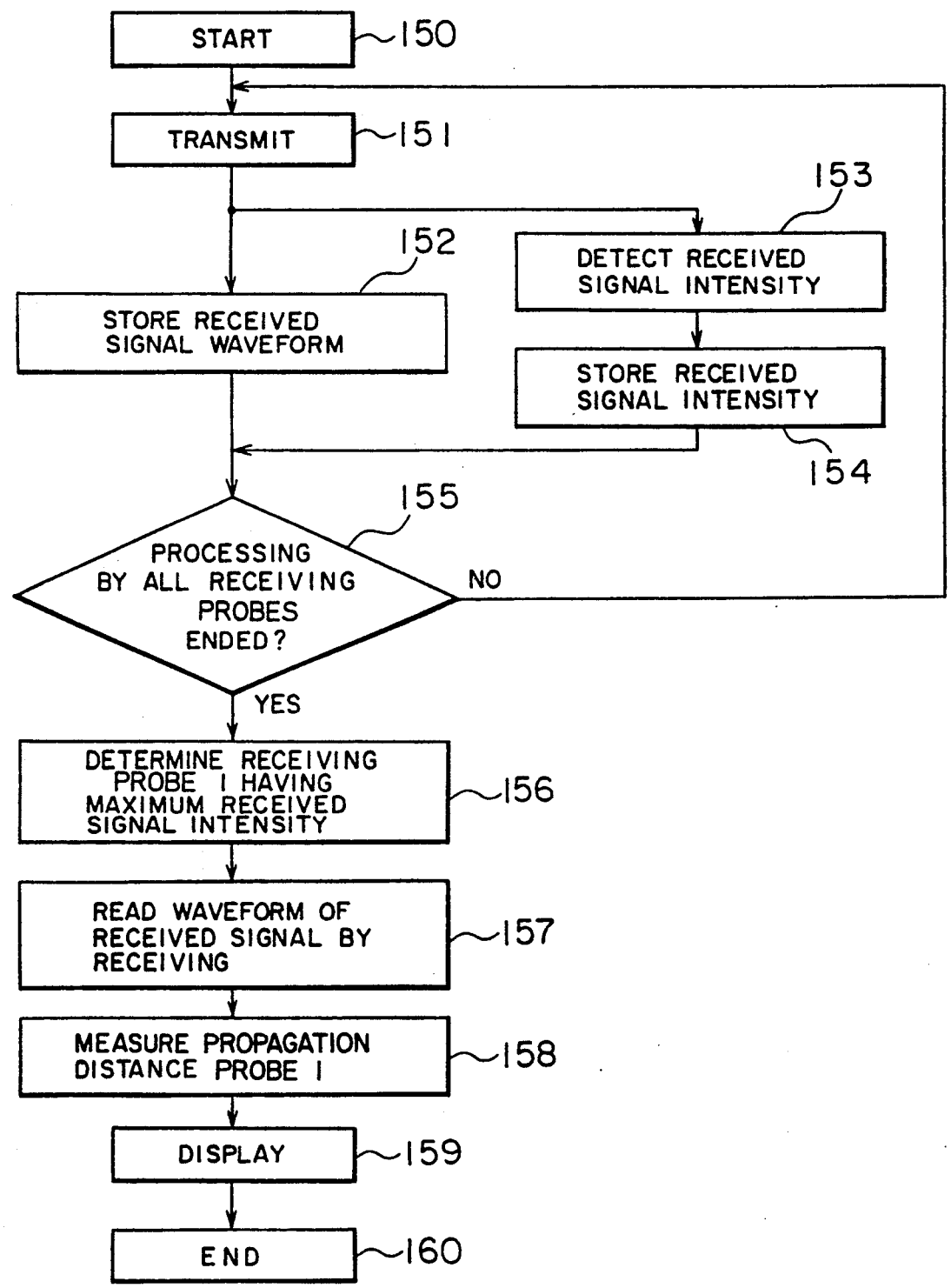
FIG. 5 is a flowchart directed to the second embodiment.

A second embodiment will be described with reference to FIGS. 4 and 5, FIG. 5 being a flowchart of the operation of the second embodiment. In FIG. 4, reference numeral 119 denotes a received-signal intensity detector; 120, a received-signal intensity memory; 121, a received-signal waveform memory; 122, a maximum received-signal intensity detector; 123, an AND gate; 103, a transmitting probe; 104, a receiving probe(-group); 105, an acoustic signal; 106, a transmitter; 107, a switch for selecting a receiving probe; and 108, a receiver. The elements 103 to 118 have substantially the same structure as the corresponding ones of the first embodiment.

In operation, the measurement error becomes substantially minimum when reception is made using a frequency where the received-signal intensity becomes maximum, as mentioned above. The FIG. 4 device measures a propagation distance using a frequency at which the received-signal intensity becomes maximum. The switch 107 connects the receiver 108 and the receiving probe i of the receiving probe group 104. First, an acoustic signal 105 is transmitted from the transmitting probe 103 into a sample in accordance with a signal transmitted from the transmitter 106 (step 151) and received by the receiving probe i. The received signal is delivered through the receiver 108 to the detector 109 where it is detected and the resulting signal is then delivered to the received-signal intensity detector 119 and the received-signal waveform memory 121. The received-signal waveform memory 121 stores data on the waveform of the received-signal and on the number i of the receiving probe which received the signal (step 152) and then the signal is delivered to the AND gate 23. Data on the received waveform can be stored either as it is or as data on the propagation time. The received-signal intensity detector 119 detects as a received-signal intensity of Pi the peak value of the signals which have exceeded the threshold value set by the threshold value setting circuit 111 in order to eliminate noise beforehand (step 153). Data on the Pi and the number i of the receiving probe used at that time are stored in the received-signal intensity memory 120 (step 154) and the signal is then delivered to the AND gate 123.

After the data are stored in the received-signal intensity memory 120 and the received-signal waveform memory 121, the two signals from the memories 120 and 121 to the AND gate causes the same to output a signal to select a receiving probe. Thus, the switch 107 selects a receiving probe ii and the received-signal intensity of Pii is calculated in a manner similar to that used in the receiving probe i (step 153) and data on the receiving probe number ii and on the received-signal intensity of Pii are stored in the received-signal intensity memory 20 (step 154) as in the receiving probe i mentioned above. Thereafter, the remaining receiving probes are sequentially selected and a similar operation is performed for each of all the remaining receiving probes (step 155). After such operation has been completed, the maximum received-signal intensity is detected by the maximum received-signal intensity detector 122 to determine the receiving probe I at that time (step 156). Data on the waveform of the received-signal corresponding to the receiving probe I is read from the received-signal waveform memory 121 (step 157) and delivered to the propagation distance measuring circuit 112, which measures the propagation distance (step 158) and the results are delivered to and displayed by the display 118 (step 159). While in the present embodiment (1) the received-signal waveform is stored, the waveform of the received-signal which will provide the maximum received-signal intensity is selected, and (2) the propagation distance is calculated, arrangement may be such that the distance is first calculated for each received-signal waveform, that the data on the distance is stored, and that data on the distance corresponding to a waveform the received-signal intensity of which becomes maximum is output as data on an accurate distance instead of storing the waveform of the received-signal.

Advantageously, the second embodiment of FIG. 4 has a simplified structure because it is unnecessary to experimentally obtain beforehand the frequency distribution of g(f) of a transmitted acoustic signal and an attenuation distribution of h(f,l) of frequencies depending on propagation distance and to store data on those distributions in memory.

Figure 6:
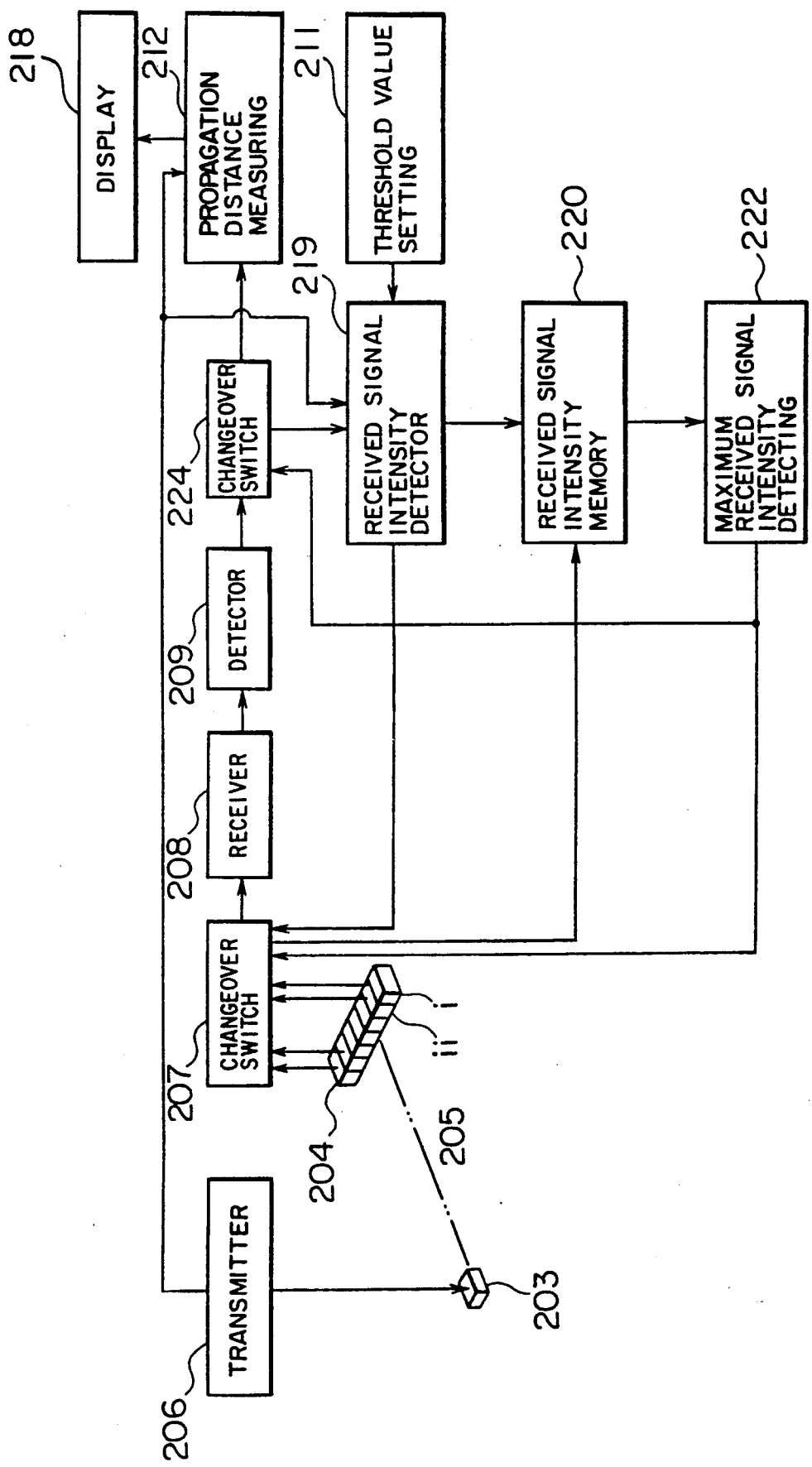
FIG. 6 schematically illustrates the structure of a third embodiment.
Figure 7:
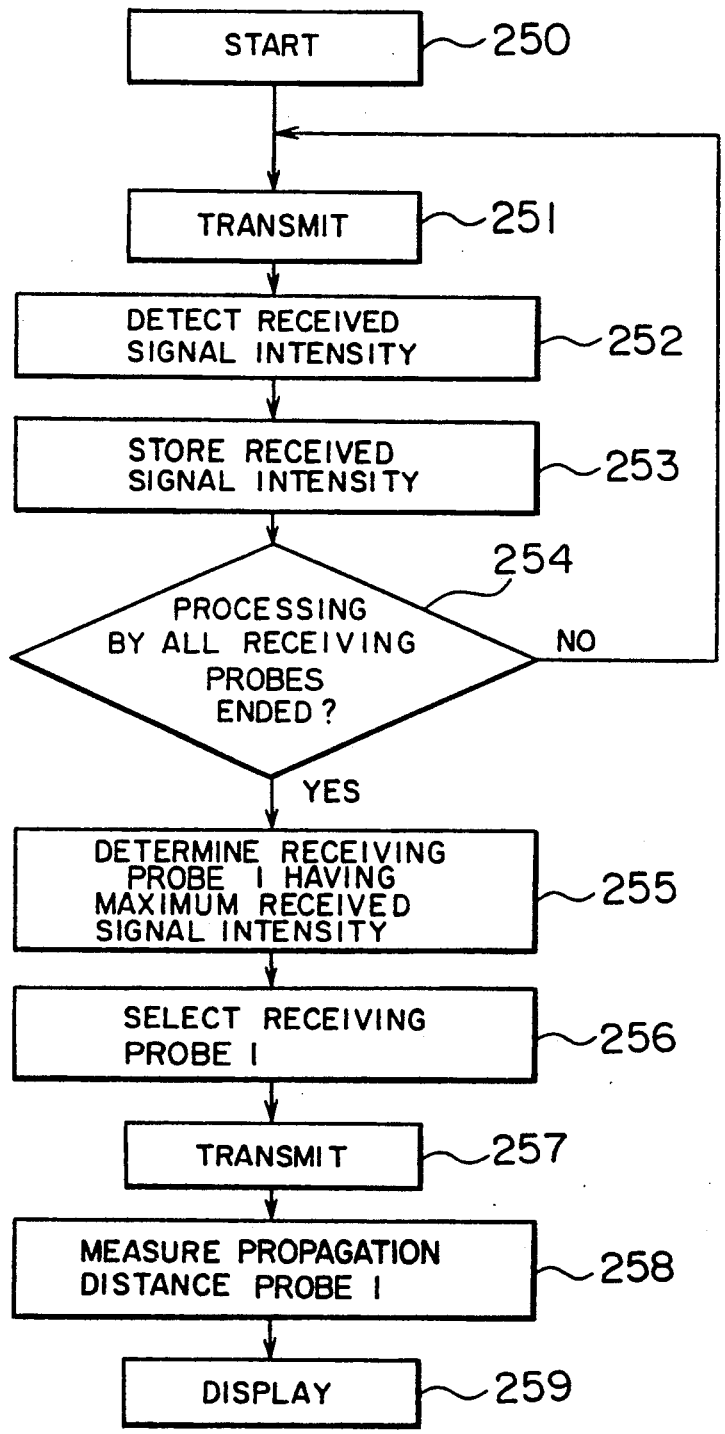
FIG. 7 is a flowchart directed to the third embodiment.

A third embodiment will be described with reference to FIGS. 6 and 7. FIG. 6 schematically illustrates the structure of a device of the present embodiment and FIG. 7 is a flowchart. In FIG. 6, reference numeral 203 denotes a transmitting probe; 204, a receiving probe (group); 205, an acoustic signal; 206, a transmitter; 207, a receiving probe selecting switch; 208, a receiver; 209, a detector; 211, a threshold value setting circuit; 212, a propagation distance measuring circuit; 218, a display; 219, a received-signal intensity detector; 220, a received-signal intensity memory; 221, a threshold value setting circuit; and 222, a maximum received-signal intensity detector; and 224, a circuit changeover switch.

The elements having reference numerals are substantially the same as those corresponding ones shown in FIGS. 1 and 4.

The third embodiment of FIG. 6 has the same structure as the second embodiment of FIG. 4 devoid of the received-signal waveform memory 121 and the AND gate 123.

The detector 209 is first connected with the received-signal intensity detector 219 by the switch 224. The transmitter probe 206 transmits an acoustic signal (step 251), the switch 207 sequentially selects the respective receiving probes of the receiving probe group 204 and the received-signal intensities are obtained at the respective receiving probes (step 252) and the data on the receiving probe numbers and the received signal intensities are stored in the received-signal intensity memory 220 (step 253). When data on all the receiving probes are stored in the received-signal intensity memory 220 (when the determining step 254 is yes), the receiving probe number I where the received-signal intensity becomes maximum in the maximum received-signal intensity detector 222 is calculated (step 255). Those procedures are the same as those in the FIG. 4 embodiment. Thereafter, in the FIG. 6 embodiment, the detector 209 and the propagation distance measuring circuit 212 are connected by the switch 224. The I-th receiving probe is selected (step 256), and again receives the transmitted acoustic signal (step 257) and the received-signal is delivered to the propagation distance measuring circuit 212, which measures the propagation distance (step 258) and delivers a signal indicative of the measured distance to the display 218 for indicating purposes (step 259).

Figure 9:
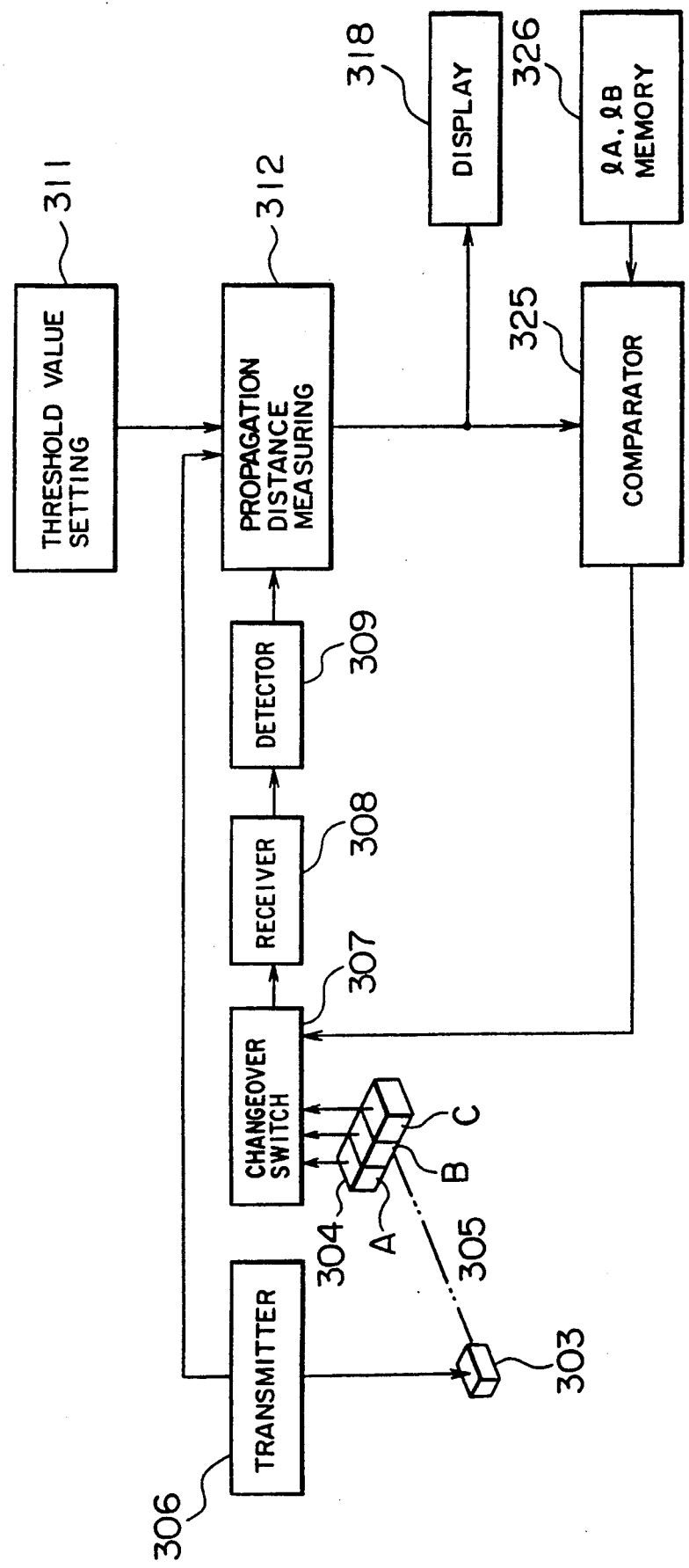
FIG. 9 schematically illustrates the structure of the fourth embodiment.
Figure 10:
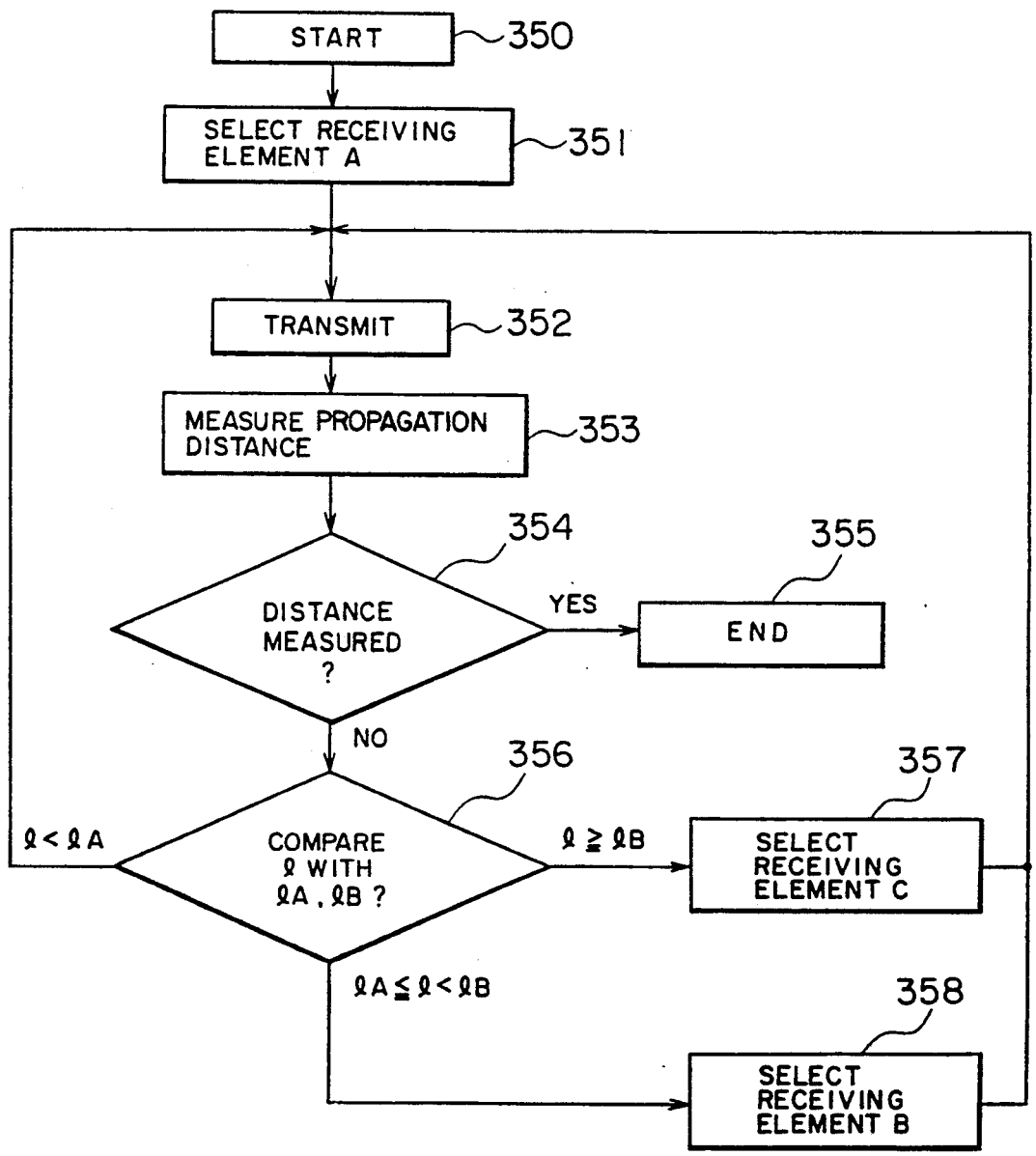
FIG. 10 is a flowchart directed to the fourth embodiment.

The concept of a fourth embodiment will be described. The first-third embodiments are used when the propagation distance between the transmitting probe and the receiving probe is not known. If the position of the wall surface vehicle for the examination of a weld line, for example, in a nuclear reactor pressure vessel is evaluated, the starting position of the vehicle is known and several receiving probes each having a different resonance frequency are used. FIG. 8A shows a relationship in that case, the use of three receiving probes 304 designated by A, B and C, and a propagation distance of $l_0$ at the start. As shown in FIGS. 8B and 8C, the relationship between the received-signal intensity of P and the time difference of $\Delta t$ for the propagation distance of $l$ in the receiving probes A, B and C are examined beforehand and $l_A$ and $l_B$ are calculated. The receiving probe A is used when the propagation distance of $l$ is between $l_0$ and $l_A$, the receiving probe B when the distance is between $l_A$ and $l_B$, and the receiving probe C when the distance is larger than $l_B$. This concept is shown in the fourth embodiment of FIG. 9, which will be described with reference to FIGS. 9 and 10, FIG. 10 being a flowchart. In FIG. 9, reference numeral 325 denotes a comparator; 326, a memory for data on $l_A$ and $l_B$. The elements denoted by the other reference numerals are substantially the same as the corresponding ones in FIGS. 1, 4 and 6.

The operation of the fourth embodiment will be described. The switch 307 connects the receiving probe A and the receiver 308 (step 351). The signal transmitted by the transmitter 306 causes the transmitting probe 303 to deliver an acoustic signal into a sample (step 352), and this signal is received by the receiving probe A. The received-signal is delivered to the detector 309 via the switch 307 and the receiver 308. After detection, the propagation distance of $l$ is measured by the propagation distance measuring circuit 312 (step 353). Data on the measured distance of $l$ is delivered to the display 318 and also to the comparator 325 which compares data on the current propagation distance of $l$ with data on $l_A$ and $l_B$ stored beforehand in the memory 326 (step 356), and a receiving probe is selected on the following conditions, as mentioned with reference to FIGS. 8B and 8C:

the receiving probe A for $l<l_A$,
the receiving probe B for $l_A \leq l < l_B$,
the receiving probe C for $l_B \leq l$.

In place of the receiving probe A, the switch 307 selects another receiving probe selected by the comparator 325 (steps 357, 358), the signal is again transmitted (step 352) and the propagation distance of $l$ is measured (step 353).

The FIG. 9 embodiment has the advantage that the examining device is able to measure the propagation distance while moving.

In the above embodiments, all the receiving probes of the receiving probe group are placed in contact with surfaces of the objects at all times.

Figure 11:
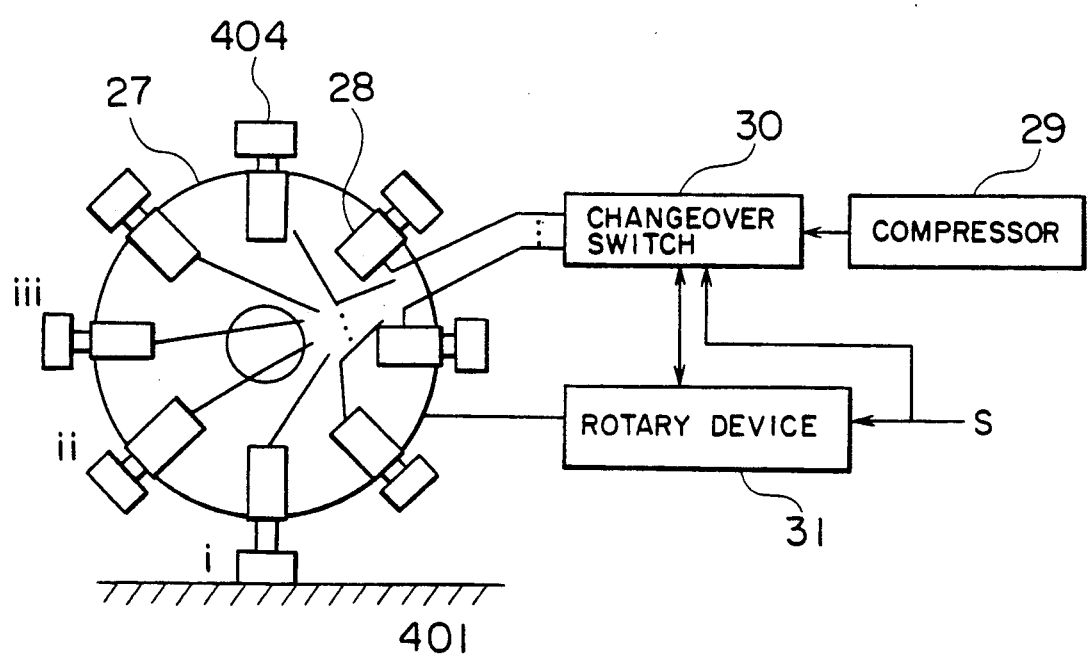
FIG. 11 schematically illustrates a fifth embodiment.

FIG. 11 schematically illustrates the structure of a fifth probe in which only a receiving probe is selected and placed in contact with a surface of a object. In FIG. 11, reference numeral 27 denotes a rotary drum; 28, an air cylinder; 29, a compressor; 30, a switch; 31, a rotary device; 404, a receiving probe; and 401, a object (to be measured). FIG. 11 illustrates that the receiving probe i is in contact with the object 401 and receiving a signal. In operation, assume that a receiving probe ii is selected in accordance with an input signal S. In response, the switch 30 temporarily stops the supply of compressed air from the compressor 29 to the air cylinder 28. Thus, the air cylinder of the receiving probe i is retracted and the receiving probe i is moved away from the object 401. Thereafter, the rotary drum 27 is rotated by the rotary device and the receiving probe ii is set at the position of the receiving probe i. Finally, the switch 30 directs the flow of compressed air to the air cylinder of the receiving probe ii. Thus, the cylinder extrudes, and the receiving probe ii comes into contact with the object 401 so as to receive an acoustic signal. While in the particular embodiment 8 receiving probes are provided, the invention is not restricted to it.

According to the fifth embodiment of FIG. 11, only one of the receiving probes is placed in contact with the object 401 and the contact area is small advantageously. In addition, selection and setting of a receiving probe is carried out easily.

Figure 12:
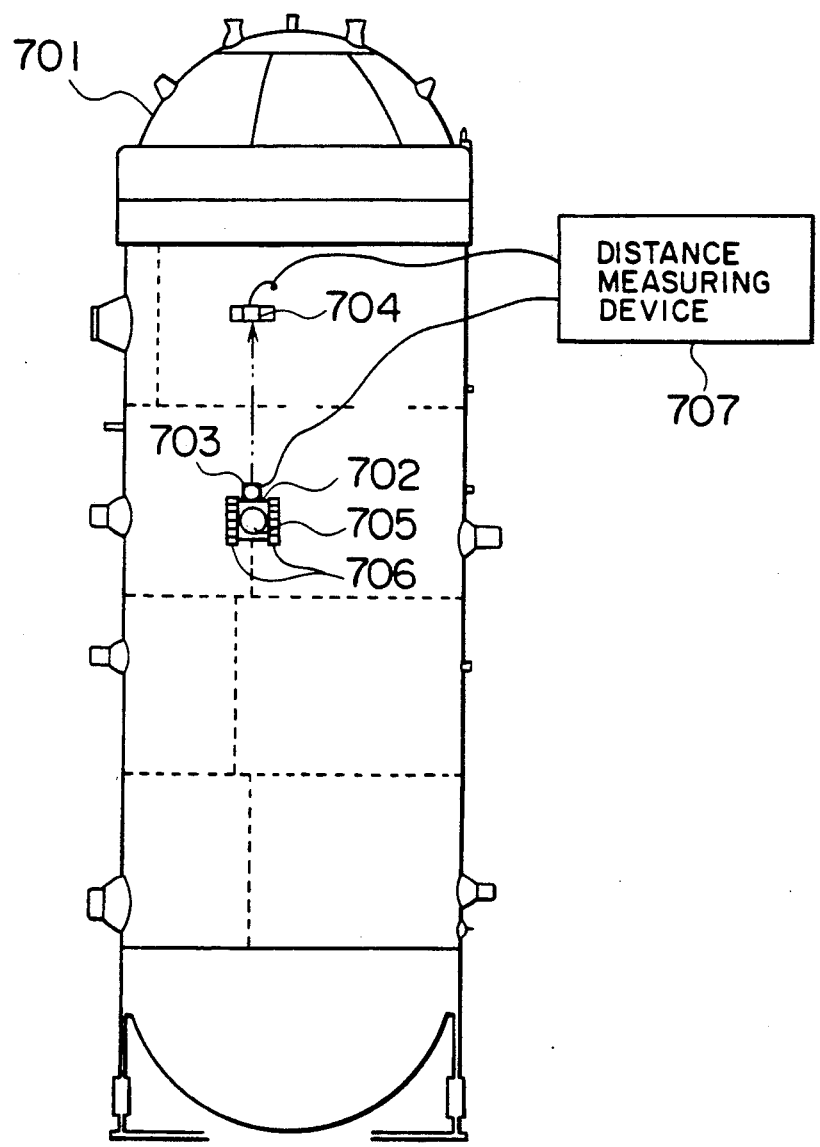
FIG. 12 illustrates a wall surface vehicle for the examination of a pressure vessel of an embodiment of the present invention.
Figure 13:
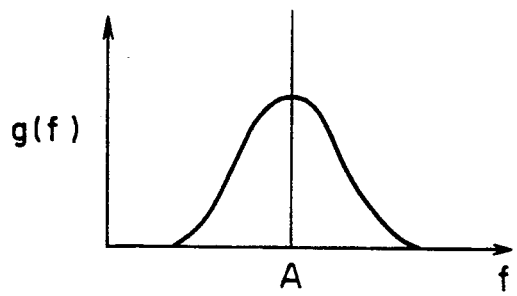
FIG. 13 is a curve indicative of the distribution of frequencies of a transmitted acoustic signal (pulse waves)
Figure 14:
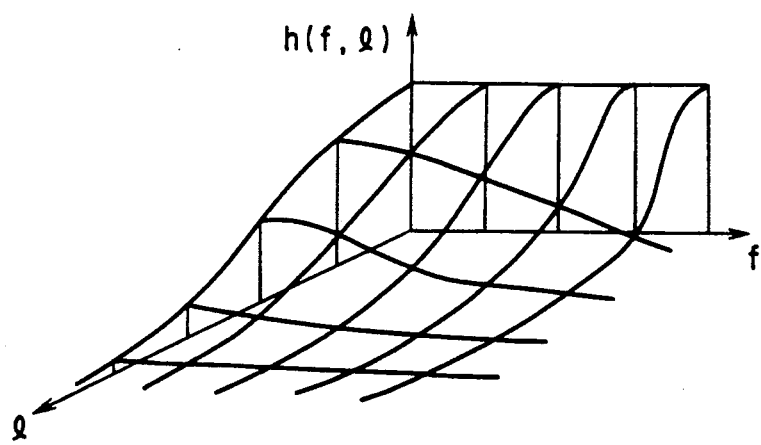
FIG. 14 shows curves illustrating the relationship between frequency, received signal intensity and propagation distance.
Figure 15:
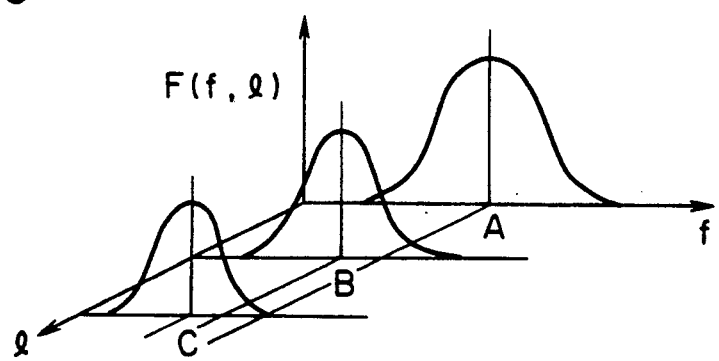
FIG. 15 is a curve indicative of a distribution of frequencies at a distance of l of a transmitted acoustic signal having a frequency distribution g(f) with a central frequency of A.
Figure 16:
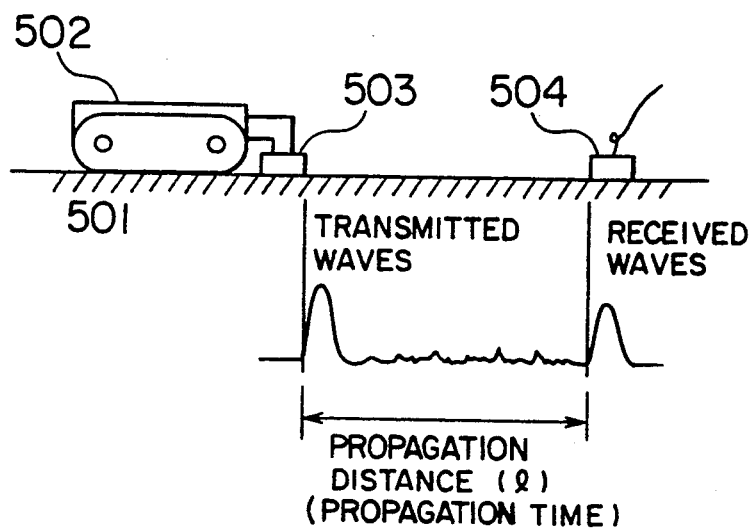
FIG. 16 illustrates a measurement of a propagation distance by the wall surface vehicle for an examination.
Figure 17A:
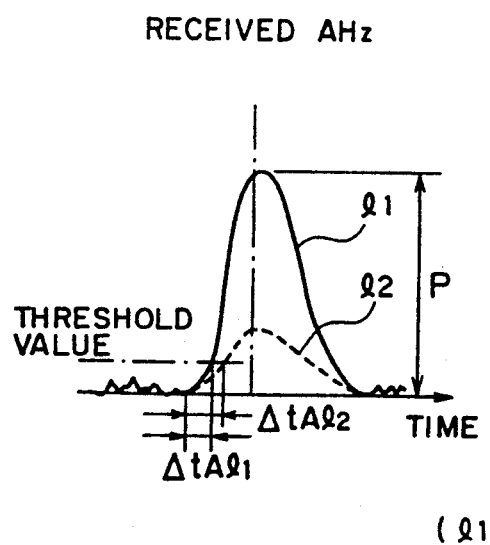
FIGS. 17A and 17B illustrate the waveforms of a received signal.
Figure 17B:
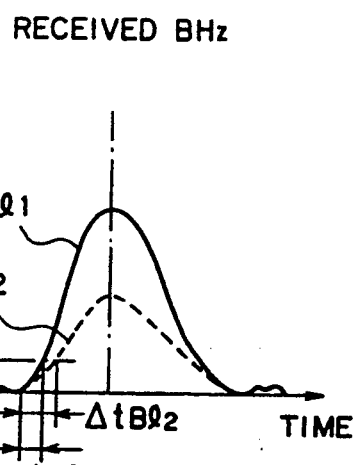
Figure 18A:
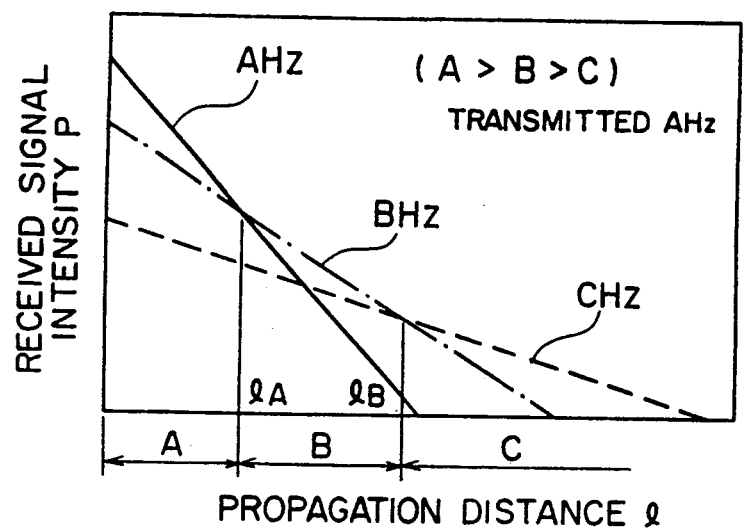
FIGS. 18A and 18B illustrate the relationship between received signal intensity, propagation distance and time difference.
Figure 18B:
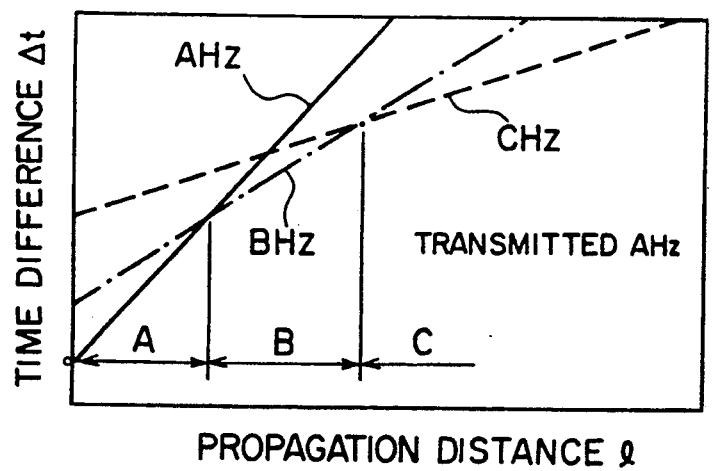
Figure 19A:
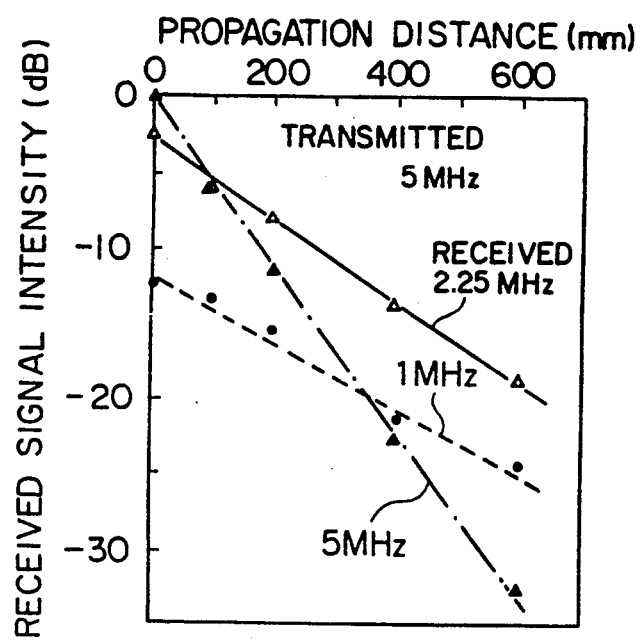
FIGS. 19A and 19B illustrate the experimentally obtained relationship between received signal intensity, propagation distance and time difference of FIGS. 18A and 18B.
Figure 19B:
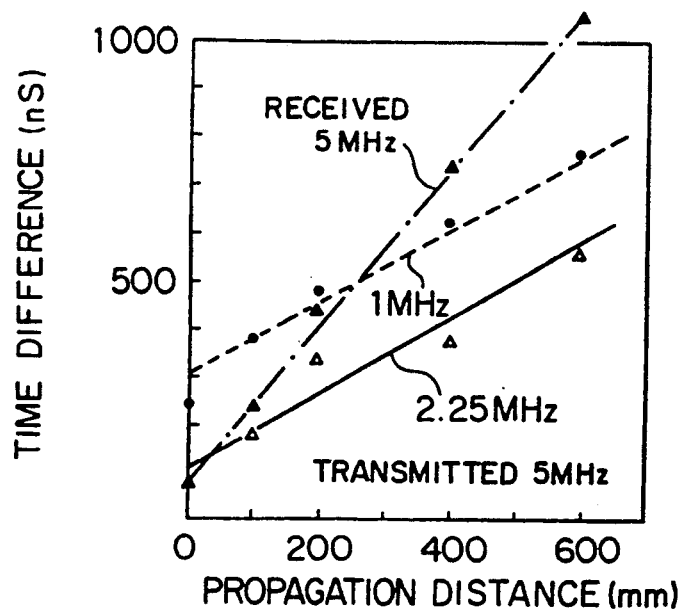

An embodiment of a wall surface vehicle for an examination (a non-destructive examination equipment) as an application of the distance measuring device according to the invention and directed to the determination as to whether a weld line in a large-sized pressure vessel is perfect or not will be described with reference to FIG. 12.

Reference numerals 701 denotes a pressure vessel which encloses the core of a nuclear reactor. The broken line in FIG. 12 denotes a weld line to be examined. A wall surface vehicle for an examination 702 has a magnetic caterpillar 706 such that it can be magnetically drawn movably to the vessel. A weld line examination equipment 705 transmits ultrasonic waves to the weld line and analyses the received reflected waves to determine whether the weld line is perfect. Reference numeral 703 denotes a transmitting probe and reference numeral 704 denotes a receiving probe (group). The transmitting and receiving probes are connected to a distance measuring device 707 in accordance with a cable system in the present embodiment. Instead, signals may be transmitted and received by radio.

The acoustic signal from the transmitting probe 703 is propagated as a surface wave through the vessel 701 and received by an optimal receiving probe of the receiving probe group, and the distance between the transmitting and receiving probes is calculated from the signal. While it is illustrated in the embodiment that the transmitting probe is disposed on the moving wall surface vehicle for the examination and the receiving probe (group) having a plurality of receiving probes is on the fixed side, it should be noted that the disposition of these probes may be selected optionally.

How to obtain or evaluate the position of the wall surface vehicle (an examined position) from the measured distance will be described. The wall surface vehicle travels along the weld line while examining it in accordance with a predetermined routine. In other words, it is on the weld line at all times. Therefore, if the distance of l between the wall surface vehicle and the receiving probe is known, the position of the wall surface vehicle is at a point of intersection of the welded line and a part of a circle having a radius of l with the receiving probe as the center. Even if the arc intersects the weld line at two or more points, the vehicle moves along the predetermined routine, as mentioned above, and it is easy to determine at which point of intersection the vehicle is located because which weld line the wall surface vehicle is on is known.

While the above is directed to disposition of the receiving probe (group) at a single point, it is conceivable that a plurality of receiving probes (groups) may be provided because the pressure vessel is large-sized. Also in this case, the position of the wall surface vehicle for the examination is at the point of intersection of the weld line and parts of circles having as radiuses the measured distances from the corresponding receiving probes (group) with the respective receiving probes as the centers.

In addition to the wall surface vehicle for the examination for pressure vessels, the present invention is applicable widely to the measurement of a long distance which causes a shift in the central frequency of the transmitted signal due to the long distance to thereby cause the frequency distribution at the reception of the signal to differ from that at the transmission. For example, the present intention is applicable to apparatuses which are self-traveled the surfaces of structures such as petroleum or gas reservoir tanks, boilers, ships, tubing, bridges or buildings, to examine, coat, assemble and repair the structures.

Unlike the above embodiments which measure the distance between the transmitting and receiving probes disposed on a surface of a structure, using a surface wave, the present invention can measure the distance (thickness) between a transmitting probe and a receiving probe disposed on the front and back sides of a solid large-sized structure using an acoustic signal in a vertical to surface of the structure.

While in the above embodiments an acoustic signal from the transmitting probe is shown and described as being received directly by the receiving probe, it should be noted that a reflected signal may be received by the receiving probe. For example, the present invention is applicable to the measurement of the depth of water or liquid in oceans and reservoir tanks by transmitting an acoustic signal from a transmitting element downward, and causing the signal to be reflected by the bottom of the ocean or tank and causing a receiving probe to receive the reflected signal, the transmitting and receiving probes being disposed close to each other with a shielding plate being disposed therebetween.

While the particular embodiment of the present invention have been shown and described, it will be obvious to those skilled in the art that various changes and modifications may be made without departing from the present invention in its broad aspects.

We claim:

1. A distance measuring apparatus comprising:
   a transmitting probe for transmitting an acoustic signal;
   a plurality of receiving probes having different resonance frequencies capable of receiving the acoustic signal from the transmitting probe;
   controlling means for controlling the transmitting probe and the receiving probes, the controlling means including selecting means for selecting one of the receiving probes and distance calculating means for calculating a propagation distance;
   wherein the controlling means enables the selecting means to select one of the receiving probes so as to receive the acoustic signal from the transmitting probe therewith, the distance calculating means calculating the propagation distance in accordance with the received acoustic signal.

2. A distance measuring apparatus according to claim 1, wherein the controlling means further includes:
   central frequency calculating means for calculating a central frequency of frequencies of the acoustic signal corresponding to the propagation distance;
   wherein the selecting means selects a receiving probe which has a resonance frequency substantially equal to the central frequency of the frequencies of the acoustic signal.

3. A distance measuring apparatus according to claim 1, wherein the controlling means further includes:
   storing means for storing the acoustic signal received by the receiving probe;
   intensity detecting means for detecting the intensity of the received acoustic signal; and
   probe detecting means for detecting in a receiving probe the intensity of the acoustic signal received which becomes a maximum among the intensities of the acoustic signal detected by the respective receiving probes selected by the selecting means;
   wherein the calculating means calculates the propagation distance from the signal received by the receiving probes at which the intensity of the detected acoustic signal becomes maximum.

4. A distance measuring apparatus according to claim 1, wherein the controlling means further includes:
   intensity detecting means for detecting the intensity of the received acoustic signals; and
   probe detecting means for detecting in the receiving probe the intensity of the acoustic signal received which becomes maximum among the intensities of the acoustic signal detected by the respective receiving probes;
   wherein the selecting means selects the detected receiving probe to enable calculation of the propagation distance.

5. A distance measuring apparatus according to claim 1, wherein the controlling means further includes:

storing means for storing a distance for selecting a receiving probe according to which the receiving probe is replaced; and comparison means for comparing the calculated propagation distance and the stored selecting distance;

wherein the selecting means selects the receiving probe which receives the acoustic signal in accordance with the stored selecting distance.

6. A distance measuring apparatus according to claim 1, wherein the selecting means includes:

a rotary device for moving any one of a plurality of the receiving probes disposed along a periphery of a disc rotatable around a central axis to a position where the one receiving probe is placed in contact with a surface of an object to be examined;

a compressor for adjusting a pressure applied to a plurality of air cylinders communicating with the respective receiving probes to thereby adjust the contact of the one receiving probe with the surface of the object; and a changeover switch for distributing a load force from the compressor such that the one receiving probe is loaded appropriately.

7. A wall surface vehicle for enabling examination, comprising a distance measuring apparatus according to claim 1.

8. A wall surface vehicle for enabling examination, comprising a distance measuring apparatus according to claim 2.

9. A wall surface vehicle for enabling examination, comprising a distance measuring apparatus according to claim 4.

10. A wall surface vehicle for enabling examination, comprising a distance measuring apparatus according to claim 5.

11. A wall surface vehicle for enabling examination, comprising a distance measuring apparatus according to claim 6.

12. A wall surface vehicle for enabling a pressure vessel examination, comprising a distance measuring apparatus according to claim 1.

13. A distance measuring method, comprising the steps of:

transmitting an acoustic signal from a transmitting probe;

selecting a receiving probe from among a plurality of receiving probes at which the intensity of the acoustic signal, changed by propagation from the transmitting probe, becomes a maximum;

receiving the signal with the selected receiving probe; and calculating a propagation distance in accordance with the received signal from the selected receiving probe.

14. A distance measuring method comprising the steps of:

transmitting an acoustic signal from a transmitting probe;

receiving the acoustic signal using a receiving probe and calculating a propagation distance;

calculating a central frequency of an optimal acoustic signal for the calculated propagation distance;

determining a receiving probe using as a resonance frequency a frequency optimal for the calculated central frequency of the acoustic signal among a plurality of receiving probes having different resonance frequencies; and receiving the signal with the determined receiving probe and calculating a propagation distance.

15. A distance measuring method comprising the steps of:

transmitting an acoustic signal from a transmitting probe;

receiving the transmitted acoustic signal by sequentially selecting a plurality of receiving probes having resonance frequencies different from the central frequency of the acoustic signal transmitted by the transmitting probe and detecting the intensities of the acoustic signals received by the respective receiving probes;

storing the respective detected intensities of the acoustic signal;

determining a receiving probe the stored intensity of the acoustic signal received by which becomes maximum among the stored intensities of the acoustic signal; and receiving the acoustic signal with the determined receiving probe and calculating a propagation distance.

16. In a distance measuring apparatus including a plurality of receiving probes having resonance frequencies different from the central frequency of a signal transmitted by a transmitting probe and a storage for storing data on distance according to which one receiving probe is replaced with another, a distance measuring method comprising the steps of:

transmitting an acoustic signal from the transmitting probe;

calculating a propagation distance from the acoustic signal received by one of the plurality of receiving probe; and comparing data on the calculated distance and data on a distance stored in the storage for replacing the receiving probe and selecting another receiving probe in accordance with distance.

* * * * *